(12) United States Patent
Sun et al.

(10) Patent No.: US 8,000,783 B2
(45) Date of Patent: Aug. 16, 2011

(54) PROCESSOR CONTROLLED VOLTAGE-CURRENT ANALYSIS FOR NERVE AND MUSCLE TISSUES

(75) Inventors: Ying Sun, Wakefield, RI (US); Jiang Wu, Norwood, MA (US); John DiCecco, Wakefield, RI (US); Robert B. Hill, Kingston, RI (US)

(73) Assignee: Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 349 days.

(21) Appl. No.: 11/500,720

(22) Filed: Aug. 8, 2006

(65) Prior Publication Data

US 2007/0038066 A1    Feb. 15, 2007

Related U.S. Application Data

(60) Provisional application No. 60/706,969, filed on Aug. 10, 2005.

(51) Int. Cl.
    *A61B 5/05* (2006.01)
(52) U.S. Cl. .................................................. 600/547
(58) Field of Classification Search ............... 600/547; 607/46
    See application file for complete search history.

(56) References Cited

U.S. PATENT DOCUMENTS

| | | | |
|---|---|---|---|
| 4,441,507 A * | 4/1984 | Steffin | ................... 600/547 |
| 4,977,895 A | 12/1990 | Tannenbaum | |
| 5,691,633 A * | 11/1997 | Liu et al. | ................... 324/71.1 |
| 6,665,562 B2 | 12/2003 | Gluckman et al. | |
| 7,334,078 B2 * | 2/2008 | Parry et al. | ................... 711/100 |
| 7,489,965 B2 | 2/2009 | Sun et al. | |
| 2005/0090865 A1 | 4/2005 | Sun et al. | |

OTHER PUBLICATIONS

Wu, Jiang, Ying Sun, Leon P. Collis and Robert B. Hill. "Modeling, Simulation and Application of a Digital Voltage Clamp for Studying Excitable Tissues." IN: Proceedings of IASTED International Conference on Applied Modelling and Simulation. 2002. p. 40-44.*
Wu, et al. "Modeling Simulation, Implementation, and Application of a Digital Voltage Clamp for Studying Excitable Tissues" p. 1-4, Nov. 4, 2002.*
Pun "Voltage clamping with single microelectrodes: Comparison of hte discontinuous and continuous mode using the Axoclamp 2A amplifier" Molecular and Cellular Biochemistry pp. 109-110.*
Wu et al. "A Universal Instrument for Biological Measurements Stimulation, Clamping, and Processing" p. 2 "References" for citation of Wu reference above.*
Nowotny et al. "StdpC Manual" copywritten 2004. pp. 1-20.*
Bekker et al. "The Axon Guide" Axon Instruments, Inc. 1993 pp. 49-51.*

* cited by examiner

Primary Examiner — Max Hlndenburg
Assistant Examiner — Renee Danega
(74) Attorney, Agent, or Firm — Gauthier & Connors LLP

(57) ABSTRACT

A device is disclosed for detecting a voltage potential from a tissue membrane. The device includes an input circuit, an output circuit and a digital signal processor. The input circuit receives a membrane voltage potential from an electrode. The output circuit receives an output command signal and provides a current output signal to the electrode. The digital signal processor is coupled to the input circuit and the output circuit. The digital signal processor provides the output command signal, and waits a delay period prior to receiving the membrane voltage signal from the input circuit.

20 Claims, 3 Drawing Sheets

PROCESSOR CONTROLLED VOLTAGE-CURRENT ANALYSIS FOR NERVE AND MUSCLE TISSUES

This application claims priority to U.S. Provisional Patent Application Ser. No. 60/706,969 filed Aug. 10, 2005.

The present invention was made with U.S. Government support under Grant (Contract) Number, R43 NS048682-01A1, awarded by the National Institute of Health. The U.S. Government has certain rights to this invention.

BACKGROUND

The present invention relates to the field of devices to study the electrophysiology of nerve and muscle tissues, and in particular to a dynamically configurable clamp device used to measure and control nerve and muscle tissues.

Voltage clamp systems are typically used in neuroscience to study the electrophysiology of nerve and muscle tissues. The relationship between current and voltage across excitable membranes are time varying, nonlinear, and spatially distributive, yielding useful information. By clamping the membrane potential to a step function, the voltage clamp system momentarily achieves spatial coherence and voltage invariance. The current injected back into the cell for maintaining a constant membrane potential may be equated to the ionic current that induces an action potential. Further decomposition of the ionic current due to sodium, potassium, and calcium may be done by ionic substitutions in the bathing solution of the tissue.

The resistance of the microelectrode as well as the cellular membrane resistance is large; on the order of megaohms. Currents associated with ion flux across a cellular membrane are quite small; on the order of nanoamperes. A short duration impulse (in microseconds) of current is passed across the membrane to establish the specified voltage. There are oscillations however, inherent to the impulse response of the system that must abate before the voltage can be sampled. In order to measure the flow of ions across the cellular membrane, it is necessary to hold the voltage of the membrane fixed, or clamped. Typically, this is accomplished by two independent microelectrodes; one to measure the current, i.e., ion flow, and the other to serve as a feedback pathway to an analog amplifier to reinforce the voltage clamp.

Another example of a prior art voltage clamp includes a single-electrode as shown in FIG. 1. The single-electrode system of FIG. 1 includes an electrode 10 that is placed in contact with a neuron, a switch 12 that selectively couples the electrode 10 to either an input voltage amplifier 14 or an output current injection unit 16. The output of the voltage amplifier 14 and the input of the current injection unit 16 are coupled to an analog feedback control unit 18, which also receive a command voltage input.

In such a single-electrode voltage clamp, the membrane potential of a neuron measured by using an electrode may be the input to a feedback control circuit. The output current may be injected back to the neuron via the same electrode. Conventionally, the voltage measurement and current injection must be decoupled by a hardware based time-multiplexing technique. The switch is used to momentarily disconnect the input to the voltage amplifier during the current injection phase, thereby avoiding potential positive feedback from the current injection to the voltage measurement.

Single-electrode voltage clamps are also disclosed in U.S. Published Patent Application Publication No. 2005/0090865. The systems disclosed in this published patent application include a digital signal processor that permit the clamp to operate in any of voltage clamp mode, current clamp mode, or a dynamic clamp mode.

Such voltage clamps, however, require that the input to a voltage amplifier be momentarily disconnected via a switch to avoid direct positive feedback from the current injection to the voltage measurement when using a single input lead. Such switching therefore, limits sampling rates.

There is a need therefore, for a system that may provide voltage clamp sampling at relatively high sampling rates using single input leads.

SUMMARY OF THE INVENTION

In accordance with an embodiment, the invention provides a device for detecting a voltage potential from a tissue membrane. The device includes an input circuit, an output circuit and a digital signal processor. The input circuit receives a membrane voltage potential from an electrode. The output circuit receives an output command signal and provides a current output signal to the electrode. The digital signal processor is coupled to the input circuit and the output circuit. The digital signal processor provides the output command signal, and waits a delay period prior to receiving the membrane voltage signal from the input circuit.

BRIEF DESCRIPTION OF THE DRAWINGS

The following description may be further understood with reference to the accompanying drawings in which.

The drawings are shown for illustrative purposes only.

DETAILED DESCRIPTION OF THE ILLUSTRATED EMBODIMENTS

The systems of various embodiments of the invention provide the ability to compensate for coupling between the voltage and current measurements. Such systems that permit feedback control of excitable tissues by using a single electrode with software based multiplexing. Since this process is digital, the voltage may be sampled at a specified point after the transient has died out. This value is the clamped voltage value and since it is held fixed, measurements of ion currents across the membrane may be made.

Figure 1:
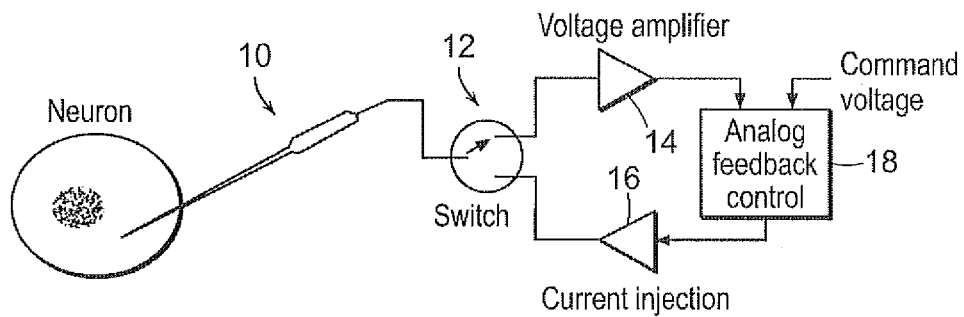
FIG. 1 shows an illustrative diagrammatic view of a prior art single-electrode voltage clamp.
Figure 2:
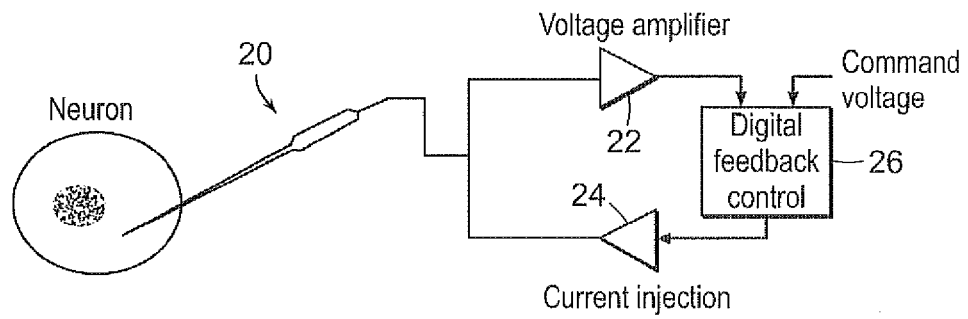
FIG. 2 shows an illustrative diagrammatic view of single-electrode voltage clamp in accordance with an embodiment of the invention.

As shown in FIG. 2, a system in accordance with an embodiment of the invention includes an electrode 20 that is directly coupled to each of an input voltage amplifier 22 as well as the output of an output current injection unit 24. The output of the voltage amplifier 22 and the input to the current injection unit 24 are coupled to a digital feedback unit 26 that also receives a voltage command signal.

Figure 3A:
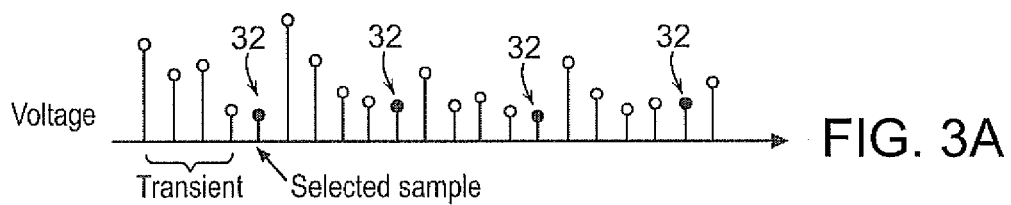
FIG. 3A shows a graphical representation of voltage triggers, transients and samples over time for a system in accordance with an embodiment of the invention.
Figure 3B:
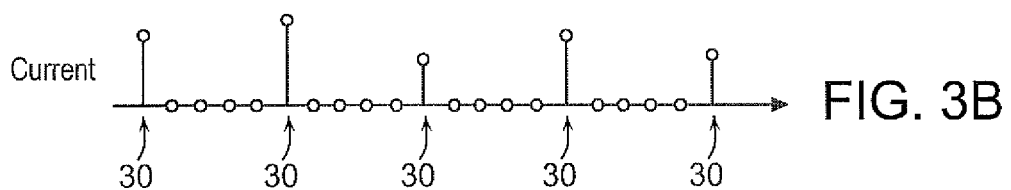
FIG. 3B shows a graphical representation of current triggers over time for a system in accordance with an embodiment of the invention.

The digital feedback unit 26 provides a software based time-multiplexing of the input and output signals. The system of FIG. 2, therefore, eliminates the need for a semiconductor switch due to the implementation of the software based time-multiplexing in the digital feedback control loop. With reference to FIGS. 3A and 3B, the transitions caused by current injections 30 are allowed to pass through, as part of the voltage input to the feedback control loop. The feedback control loop implemented with a digital signal processor (DSP) however, selectively uses only voltage samples 32 from time instances when transients have subsided (for example, after about 1 to 10 samples or about 1 to 10 microseconds depending on the experimental preparation). Decoupling is done under software control by selectively using the appropriate voltage samples (black dots) to avoid transients caused by the current injection. The injected current is limited to a safe level to avoid damage to the voltage amplifier. This software switched control may be implemented at a high sampling rate on the order of about 1 MHz. The membrane potential of the neuron may be controlled by frequent injections, with relatively small amount of current per injection. In further embodiments, the system may monitor the pattern of transient signals after certain times during the delay period.

Various applications of such systems include the area of functional electrical stimulation in which currents are injected via electrodes to stimulate muscles in paralyzed limbs. Systems of the invention may provide better controls of the current injections by using induced potentials as feedback. In the area of brain-machine interface, the systems of the invention provide new opportunities to dynamically control the current stimuli to neurons in the sensory cortex, peripheral nerves, or skeletal muscles.

Figure 4A:
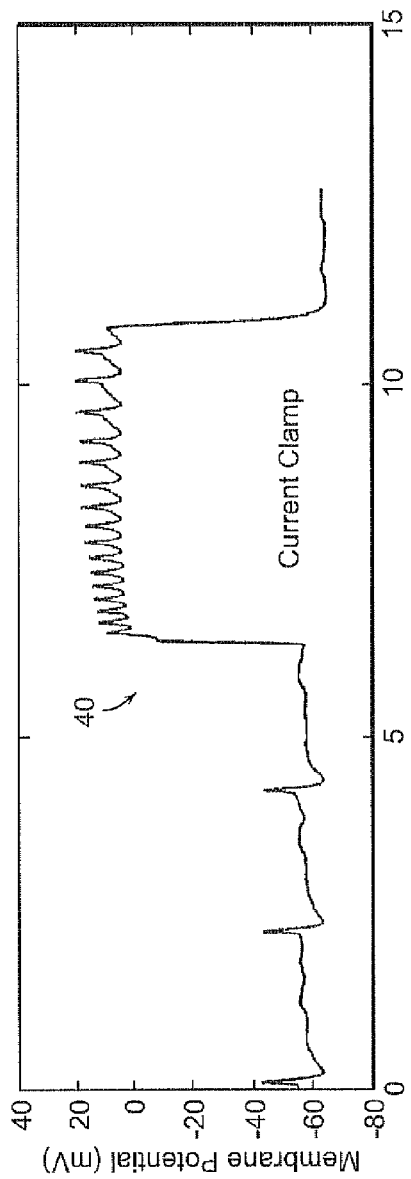
FIGS. 4A and 4B show graphical representations of membrane potentials for a current clamp and a voltage clamp respectively over time for a system in accordance with an embodiment of the invention.
Figure 4B:
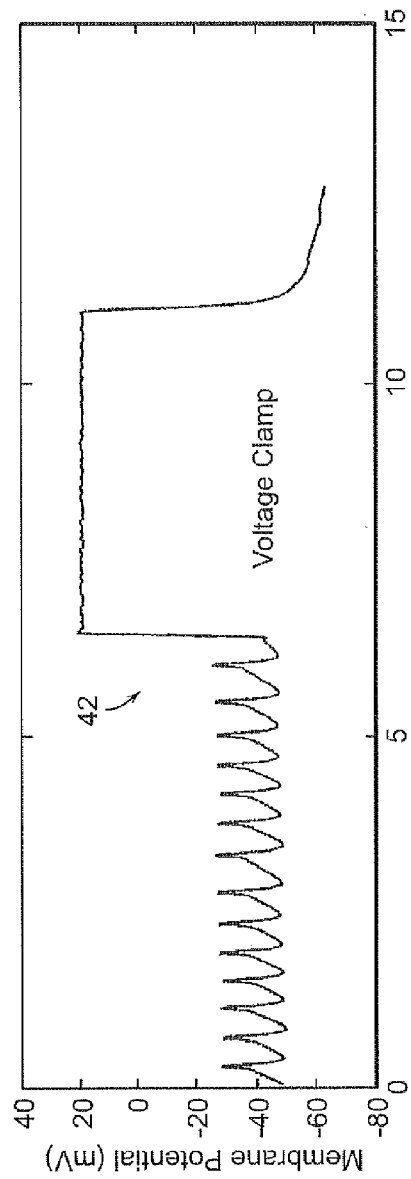

The software switched single-electrode voltage clamp may be implemented in the DSP chip of a universal clamp system as disclosed in U.S. Published Patent Application Publication No. 2005/0090865, the disclosure of which is hereby incorporated by reference. Successful preliminary results have been obtained from experiments with neurons of the pond snail (*Lymnaea stagnalis*) and the sea slug (*Alysia californica*). FIG. 4A shows at 40 the membrane potential over time for a current clamp and FIG. 4B shows at 42 the membrane potential over time for a single-electrode voltage clamp for the pond snail. The universal clamp was used to inject a rectangular waveform of depolarization current into a neuron of the pond snail via a microelectrode. The depolarization caused increased firing rate of the action potentials. With respect to FIG. 4B, the software switched voltage clamp was turned on at the same time using the same preparation. The universal clamp is, therefore, usable to clamp the membrane potential at 20 mV, eliminating the firing of the action potentials during the depolarization period. The results indicate that the system of the invention may successfully clamp the membrane potential to the desired voltage level and eliminate the firing of action potentials.

Figure 5:
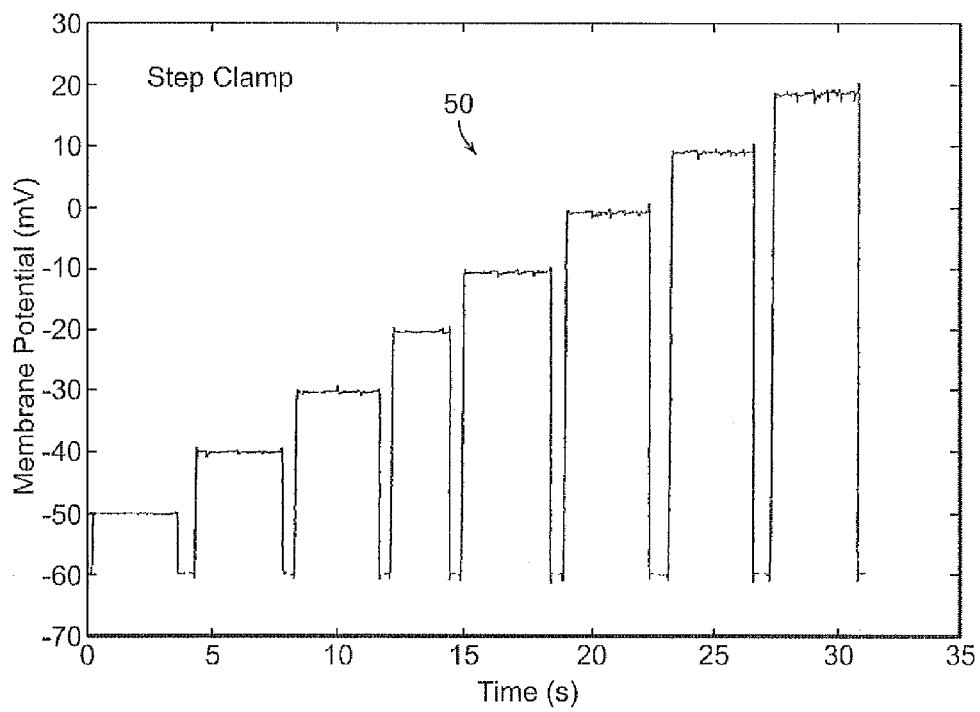
FIG. 5 shows a graphical representation of step clamp operation of a sample in accordance with an embodiment of the invention.

FIG. 5 shows at 50 the membrane potential versus time for a step clamp result that was obtained using a system of the invention with neurons of a sea slug. The resting membrane potential was −60 mV. By use of the universal clamp, the membrane potential was clamped from −50 mV to 20 mV at a step of 10 mV. The proposed method may accurately clamp the membrane potential to the desired voltage steps, with results that are comparable to the conventional two-electrode voltage clamp.

The software allows the investigator to measure cellular ionic flux and/or control the membrane potential with one microelectrode instead of two. There are inherent difficulties in inserting two electrodes into one cell, most notably the likelihood of dislodging the first microelectrode by attempting to insert the second. Additionally, no further cellular damage is incurred at the expense of inserting a second electrode, a very desirable result when attempting to accurately explain the physiology of an intact cell. As the acquired data is in the digital format, the data is more readily processed and programming time series experiments can be achieved with much greater precision and control. Systems of the invention eliminate the need for a hardware switch to time-multiplex voltage measurement and current injection. The software switched voltage-current feedback control will improve instrumentation in the areas of neurophysiological research, functional electrical stimulation, and brain-machine interface.

Those skilled in the art will appreciate that numerous modifications and variations may be made to the above disclosed embodiments without departing from the spirit and scope of the invention.

What is claimed is:

1. A device for controlling a voltage potential from a tissue membrane, said device comprising:
   an input circuit that receives a membrane voltage potential from an electrode;
   an output circuit that receives an output command signal and injects a current output signal directly to said electrode without going through any hardware switch; and
   a digital signal processor coupled to both the input circuit and the output circuit, said digital signal processor for providing said output command signal in the form of discrete pulses, and for permitting reception of said membrane voltage signal from said input circuit at any of a plurality of reception times during a delay period at a sample rate following providing said output command signal.

2. The device as claimed in claim 1, wherein said delay period is adaptive to said input membrane potential and is between about 1 sample and about 10 samples, and wherein the sample rate is about 1 MHz.

3. The device as claimed in claim 1, wherein said delay period is adaptive between about 1 microsecond and about 10 microseconds.

4. The device as claimed in claim 1, wherein said input circuit and said output circuit are directly coupled together at the electrode without going through any hardware switch.

5. The device as claimed in claim 1, wherein said digital signal processor continuously samples input signals and selectively uses an input signal for feedback control immediately after the delay period to avoid the transient caused by the previous current feedback pulse.

6. The device as claimed in claim 1, wherein said device provides at least one of a voltage clamp, a current clamp, a dynamic clamp, or a patch clamp.

7. The device as claimed in claim 1, wherein software in said digital signal processor selectively bypasses periodic transients caused by the injected current pulse thereby time-multiplexing an input and an output in a single electrode without using a hardware switch.

8. The device as claimed in claim 1, wherein said digital signal processor provides a sampling rate on the order of about 1 MHz.

9. A device for controlling a voltage potential from a tissue membrane, said device comprising:
   an input circuit that receives a membrane voltage potential from an electrode at a first node;

an output circuit that receives an output command signal and injects a current output signal directly to said electrode at the first node without going through any hardware switch; and a digital signal processor coupled to both the input circuit and the output circuit, said digital signal processor for providing said output command signal in the form of discrete pulses, and for permitting reception of said membrane voltage signal from said input circuit at any of a plurality of reception times during a delay period at a sample rate that provides the plurality of reception time during the delay period including and following providing said output command signal.

10. The device as claimed in claim 9, wherein said delay period is adaptive to said input membrane potential and is between about 1 sample and about 10 samples, and wherein the sample rate is about 1 MHz.

11. The device as claimed in claim 9, wherein said delay period is adaptive between about 1 microsecond and about 10 microseconds.

12. The device as claimed in claim 9, wherein said digital signal processor continuously samples input signals and selectively uses an input signal for feedback control immediately after the delay period to avoid transients caused by a previous feedback output pulse.

13. The device as claimed in claim 9, wherein said device provides at least one of a voltage clamp, a current clamp, a dynamic clamp, or a patch clamp.

14. The device as claimed in claim 9, wherein software in said digital signal processor selectively bypasses periodical transients caused by the injected current pulse, thereby time-multiplexing input and output in a single electrode without using any hardware switch.

15. The device as claimed in claim 9, wherein said digital signal processor provides a sampling rate of about 1 MHz.

16. A method for controlling a voltage potential from a tissue membrane, said method comprising the steps of:

providing an output command signal from a digital signal processor to an output circuit;

injecting a current output signal directly to an electrode at a first node from the output circuit responsive to the output command signal without going through any hardware switch;

permitting reception of a membrane voltage potential from the electrode at the first node at each of a plurality of reception times during a delay period at a sample rate that provides the plurality of reception times during the delay period following providing the current output signal to the electrode;

selecting from the plurality of reception times a selected reception time for receiving the membrane voltage potential from the electrode; and providing the membrane voltage potential to the digital signal.

17. The method as claimed in claim 16, wherein said delay period is adaptive to said input membrane potential and is between about 1 sample and about 10 samples.

18. The method as claimed in claim 16, wherein said delay period is adaptive between about 1 microsecond and about 10 microseconds.

19. The method as claimed in claim 16, wherein said digital signal processor continuously samples input signals and selectively uses an input signal for feedback control immediately after the delay period to avoid transients caused by a previous current feedback output pulse.

20. The method as claimed in claim 16, wherein the sampling rate is on the order of about 1 MHz.

* * * * *

UNITED STATES PATENT AND TRADEMARK OFFICE
CERTIFICATE OF CORRECTION

| | | |
|---|---|---|
| PATENT NO. | : 8,000,783 B2 | Page 1 of 1 |
| APPLICATION NO. | : 11/500720 | |
| DATED | : August 16, 2011 | |
| INVENTOR(S) | : Sun et al. | |

It is certified that error appears in the above-identified patent and that said Letters Patent is hereby corrected as shown below:

In the Specification

Column 1, lines 7-10, please replace the current clause with the following:

"This invention was made with government support under Grant No. R43 NS048682 awarded by the National Institutes of Health. The government has certain rights in the invention."

Signed and Sealed this
Eighteenth Day of August, 2015

Michelle K. Lee
*Director of the United States Patent and Trademark Office*